(12) United States Patent
Kim et al.

(10) Patent No.: US 6,489,268 B1
(45) Date of Patent: Dec. 3, 2002

(54) HIGHLY SELECTIVE HERBICIDAL PHENOXYPROPIONIC ACID ALKOXYCARBONYL ANILID COMPOUNDS AND METHOD OF PREPARING THE SAME

(75) Inventors: Dae Whang Kim, Daejeon (KR); Hae Sung Chang, Daejeon (KR); Young Kwan Ko, Daejeon (KR); Jae Wook Ryu, Daejeon (KR); Jae Chun Woo, Daejeon (KR); Dong Wan Koo, Daejeon (KR); Tae-Joon Kim, Daejeon (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 0 days.

(21) Appl. No.: 10/048,172

(22) PCT Filed: Jul. 31, 2000

(86) PCT No.: PCT/KR00/00834
§ 371 (c)(1),
(2), (4) Date: Jan. 29, 2002

(87) PCT Pub. No.: WO01/08479
PCT Pub. Date: Feb. 8, 2001

(30) Foreign Application Priority Data

Aug. 3, 1999  (KR) ............................................. 99-31855

(51) Int. Cl.$^7$ ........................ A01N 43/76; C07D 263/58
(52) U.S. Cl. ....................................... 504/270; 548/221
(58) Field of Search ........................... 548/221; 504/270

(56) References Cited

U.S. PATENT DOCUMENTS

| | | |
|---|---|---|
| 4,130,413 A | 12/1978 | Handte et al. |
| 4,531,969 A | 7/1985 | Nestler et al. |
| 4,968,343 A | 11/1990 | Turner et al. |
| 5,254,527 A | 10/1993 | Nestler et al. |

FOREIGN PATENT DOCUMENTS

| | | |
|---|---|---|
| DE | 2245471 | 3/1973 |
| EP | 0527016 | 2/1993 |
| JP | 2-11580 | 1/1990 |

OTHER PUBLICATIONS

English–Language Abstract of JP 2–11580.

G. Snatzke et al., Determination of the Optical Purity of Substituted N–phenylpropionamides by NMR Spectroscopy. Org. Magn. Resonance, May 1, 1973 (9), 413–14 (Eng.) Columbus OH USA: Chemical Abstracts vol. 80, p. 262, col. 2, the Abstract No. 2990y.

M. A. Sayed et al., Synthesis and Some Reactions of 2–(chloroethyl)–3, 1–nenzoxazin–4(H). One Indian J. Chem. Sect. B, Mar. 1, 1991 OB (10); 980–3 (Eng). Columbus OH USA: Chemical Abstracts vol. 115, p. 859, col. 1, the abstract No. 256110h.

P. Singh et al., Study in Nitrogen Mustards, Part III. Synthesis of some 2–alkyl–3–aryl–4 (3)–quinazolinone Derivatives with Nitrogen Mustard Moiety as Possible Antitumor Agents, J. Indian Chem. Soc., May 1, 1979 6 (1) 77–80 (Eng). Columbus OH USA: Chemical Abstracts vol. 92, p. 669, col. 1, the abstract No. 58712z.

Snatzke, G–et al. –Synthesis of Optically active alpha–halopropion–anilides–Chem– Ber–, Oct. 1, 1973, 6 (6), 2072–5 (Ger–)– Columbus OH USA: Chemical Abstracts vol. 79, p. 399, col. 2, the abstract No. 65754z.

I. Hermecz et al., Nitrogen Bridgehead Compounds. Part 85, Synthesis and Reactivity of 3, 4–dihydro–1H, 6H. [1,4] oxazino[3,4.b]quiazolin–6–ones, J. Heterocycl. Chem. 1993, 30(5), 1413–20 (Eng). Columbus OH USA: Chemical Abstracts vol. 120, p. 1039, col. 2, the abstract No. 245002b.

*Primary Examiner*—Robert W. Ramsuer

(57) ABSTRACT

The present invention relates to high selective herbicidal phenoxypropionic acid alkoxycarbonyl anilid compounds represented in formula 1, method of preparing thereof, their use to control barnyard grass produced from rice, and a composition as suitable herbicides, (1)

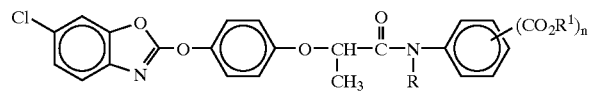

wherein

R is a hydrogen atom, methyl or ethyl group;

$R^1$ is a hydrogen atom, $C_1$–$C_6$ alkyl, $C_1$–$C_6$ alkyl substituted with 1 to 3 of the group consisting of hydroxy, carboxyl, and a halogen atom, $C_3$–$C_6$ cycloalkyl, $C_3$–$C_4$ alkenyl, $C_3$–$C_4$ alkinyl, or $C_2$–$C_4$ alkoxyalkyl group;

n is an integer of 1 or 2 and when n is 2, $R^1$ can be a combination of other substituents.

19 Claims, No Drawings

HIGHLY SELECTIVE HERBICIDAL PHENOXYPROPIONIC ACID ALKOXYCARBONYL ANILID COMPOUNDS AND METHOD OF PREPARING THE SAME

This application is a 371 of PCT/KR00/00834 filed Jul. 31, 2000

BACKGROUND OF THE INVENTION

1. Field of the Invention

The present invention relates to high selective herbicidal phenoxypropionic acid alkoxycarbonyl anilid compounds represented in formula 1, method of preparing thereof, their use to control barnyard grass produced from rice, and a composition as suitable herbicides,

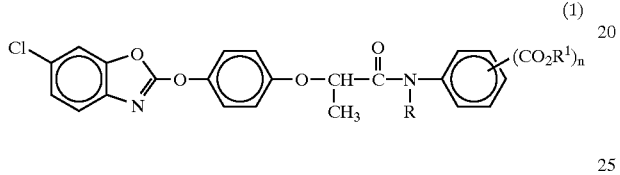

(1)

wherein

R is a hydrogen atom, methyl or ethyl group;

$R^1$ is a hydrogen atom, $C_1$–$C_6$ alkyl, $C_1$–$C_6$ alkyl substituted with 1 to 3 of the group consisting of hydroxy, carboxyl, and a halogen atom, $C_3$–$C_6$ cycloalkyl, $C_3$–$C_4$ alkenyl, $C_3$–$C_4$ alkinyl, or $C_2$–$C_4$ alkoxyalkyl group;

n is an integer of 1 or 2 and when n is 2, $R^1$ can be a combination of other substituents.

2. Description of the Prior Art

U.S. Pat. No. 4,130,413 disclosed the compound represented in the following formula 2,

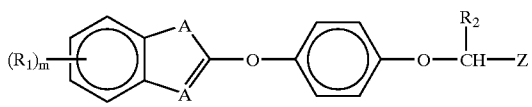

(2)

wherein $(R_1)_m$ is a hydrogen atom, a halogen atom, $CF_3$, $NO_2$, CN or alkyl group;

A is O, S or NH;

$R_2$ is a hydrogen atom or alkyl group; and

Z is

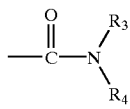

(wherein $R_3$ and $R_4$, that are the same or different, are a hydrogen atom, $C_1$~$C_6$ alkyl, $C_1$~$C_6$ hydroxyalkyl, $C_3$~$C_6$ cycloalkyl, $C_1$~$C_4$ alkoxy, or phenyl substituted with 1 to 3 substituents selected from the group consisting of $C_1$~$C_4$ alkyl group, $C_1$~$C_6$ alkoxy group, a halogen atom and $CF_3$.

U.S. Pat. No. 4,531,969 disclosed the compounds represented in the following formula 3,

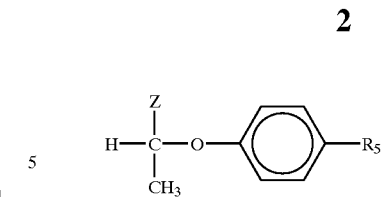

(3)

wherein $R_5$ is

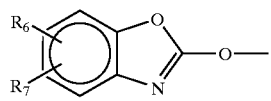

(where $R_6$ is a hydrogen or a halogen atom, $R_7$ is a hydrogen atom or alkyl group); Z is the same as defined above.

U.S. Pat. No. 5,254,527 disclosed the compounds represented in the following formula 4,

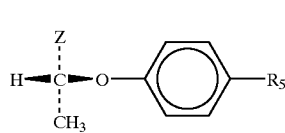

(4)

wherein, $R_5$ and Z are the same as defined above.

Japanese Patent publication 2-11580 disclosed the compounds represented in the following formula 5,

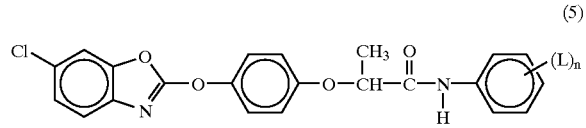

(5)

wherein L is lower alkyl group, a halogen atom, methoxy, methoxyphenoxy, benzyloxy, methylthio, methylvinyl group; and n is an integer of 0 to 3.

U.S. Pat. No. 4,968,343 disclosed the compounds represented in the following formula 6.

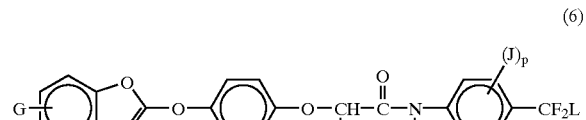

(6)

Japanese Patent publication 53-40767 and 54-112828 also disclosed that phenoxypropionic acid amide derivatives show herbicidal activities.

However, none of the patents teaches the synthesis of the compound represented in the above formula 1 and has tested the same for herbicidal activity. Furthermore, it has not been reported that the compounds have superior herbicidal activity and selectivity toward rice and control barnyard grass produced from rice.

SUMMARY OF THE INVENTION

Even though many of herbicides for rice have been recently developed and used, barnyard grass among weeds is the biggest problem in rice paddy.

Development of herbicides to control barnyard grass is an urgent request to one who is in the field of agriculture. After transplanting young rice, conventional herbicides, developed until now, cannot effectively control the production of barnyard grass so that it causes a huge damage to harvest. It has been reported that when barnyard grass is produced for one week in 1 m$^2$, amount of harvest decreases by 2%, for 5 weeks by about 10%, for 10 weeks by 19% and for 20 weeks by 35%.

Many herbicides have been used for the purpose of controlling barnyard grass that damages in huge amount of harvest of rice. However, the herbicide with a broader herbicidal activity, environmentally-friendly property and cost-effectiveness is still in demand.

The inventors have intensively studied to prepare herbicides to effectively control barnyard grass. As a result, we completed this invention to find a novel phenoxypropionic acid alkoxycarbonyl anilid and its derivatives that are stable to rice and selectively control barnyard grass. This superior effectiveness is distinguished from the conventional inventions.

DETAILED DESCRIPTION OF THE INVENTION

The present invention is characterized by novel phenoxypropionic acid alkoxy-carbonyl anilid and its derivatives represented in formula 1 with an excellent herbicidal activity as well as selectively stable toward rice.

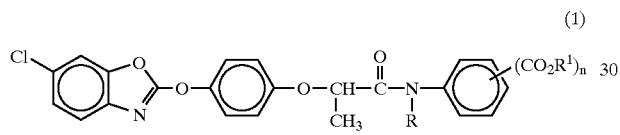

(1)

wherein, R, R$^1$, and n are the same as previously defined.

The compounds of formula 1 according to the present invention may be specified as the following Table 1.

TABLE 1

(1)

| R | n | Substituted position of CO$_2$R$^1$ | R$^1$ |
|---|---|---|---|
| H | 1 | 3 | H |
| H | 1 | 3 | CH$_3$ |
| H | 1 | 3 | CH$_2$CH$_2$Cl |
| H | 1 | 3 | CH$_2$CH$_3$ |
| H | 1 | 3 | CH$_2$CH$_2$CH$_3$ |
| H | 1 | 3 | CH(CH$_3$)$_2$ |
| H | 1 | 3 | (CH$_2$)$_3$CH$_3$ |
| H | 1 | 4 | H |
| H | 1 | 4 | CH$_3$ |
| H | 1 | 4 | CH$_2$CH$_3$ |
| H | 1 | 4 | CH$_2$CH$_2$Cl |
| H | 1 | 4 | CH$_2$CH$_2$CH$_3$ |
| H | 1 | 4 | CH(CH$_3$)$_2$ |
| H | 1 | 4 | (CH$_2$)$_3$CH$_3$ |
| H | 1 | 2 | H |
| H | 1 | 2 | CH$_3$ |
| H | 1 | 2 | CH$_2$CH$_3$ |
| H | 1 | 2 | CH$_2$CH$_2$Cl |
| H | 1 | 2 | CH$_2$CH$_2$CH$_3$ |
| H | 1 | 2 | CH(CH$_3$)$_2$ |
| H | 1 | 2 | (CH$_2$)$_3$CH$_3$ |
| H | 2 | 3, 4 | CH$_3$ |
| H | 2 | 3, 4 | CH$_2$CH$_3$ |
| H | 2 | 2, 3 | CH$_3$ |

TABLE 1-continued (1)

| R | n | Substituted position of CO$_2$R$^1$ | R$^1$ |
|---|---|---|---|
| CH$_3$ | 1 | 2 | H |
| CH$_3$ | 1 | 2 | CH$_3$ |
| CH$_3$ | 1 | 3 | H |
| CH$_3$ | 1 | 3 | CH$_3$ |
| CH$_3$ | 1 | 3 | CH$_2$CH$_3$ |
| CH$_3$ | 1 | 3 | CH$_2$CH$_2$Cl |
| CH$_3$ | 1 | 3 | CH$_2$CH$_2$CH$_3$ |
| CH$_3$ | 1 | 3 | CH(CH$_3$)$_2$ |
| CH$_3$ | 1 | 3 | (CH$_2$)$_3$CH$_3$ |
| CH$_2$CH$_3$ | 1 | 3 | CH(CH$_3$)$_2$ |
| CH$_3$ | 1 | 4 | H |
| CH$_3$ | 1 | 4 | CH$_3$ |
| CH$_3$ | 1 | 4 | CH$_2$CH$_3$ |
| CH$_3$ | 1 | 4 | CH$_2$CH$_2$CH$_3$ |
| CH$_3$ | 1 | 4 | (CH$_2$)$_3$CH$_3$ |
| CH$_3$ | 1 | 4 | CH(CH$_3$)$_2$ |
| CH$_3$ | 2 | 2, 3 | CH$_3$ |
| CH$_3$ | 2 | 2, 3 | CH$_2$CH$_3$ |
| CH$_3$ | 2 | 3, 4 | CH$_3$ |
| CH$_3$ | 2 | 3, 4 | CH$_2$CH$_3$ |
| H | 1 | 3 | cyclopropyl |
| H | 1 | 4 | cyclopropyl |
| H | 1 | 3 | cyclopropylmethyl |
| H | 1 | 4 | cyclopropylmethyl |
| H | 1 | 3 | cyclohexyl |
| H | 1 | 3 | CH$_2$CH=CH$_2$ |
| H | 1 | 3 | CH$_2$—C≡CH |
| H | 1 | 4 | CH$_2$CH=CH$_2$ |
| H | 1 | 4 | CH$_2$C≡CH |
| H | 1 | 3 | CH$_2$CH$_2$OCH$_3$ |
| H | 1 | 4 | CH$_2$CH$_2$OCH$_3$ |
| H | 1 | 3 | CH2CH$_2$OH |
| H | 1 | 4 | CH2CH$_2$OH |
| H | 1 | 3 | CH$_2$CO$_2$H |
| H | 1 | 3 | CH$_2$CO$_2$CH$_3$ |
| H | 1 | 4 | CH$_2$CO$_2$H |
| H | 1 | 4 | CH$_2$CO$_2$CH$_3$ |
| H | 1 | 3 | CH$_2$CO$_2$Et |
| H | 1 | 4 | CH$_2$CO$_2$Et |

The compounds of formula 1 according to the present invention can be synthesized by a conventional method represented in the following scheme 1, reacting a compound of formula 7 with a compound of formula 8.

Scheme 1

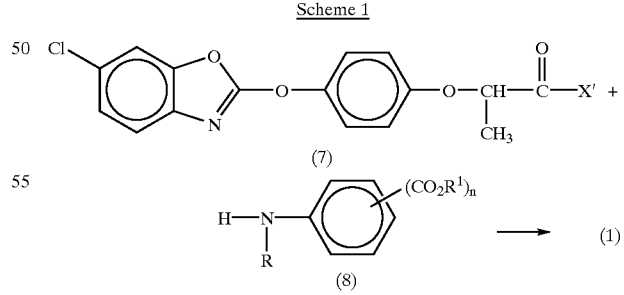

wherein X$^1$, which is a leaving group, is OH, Cl, Br or phenoxy group; R, R$^1$ and n are the same as previously defined.

In the method according to scheme 1, condensation reaction can be performed by using binder such as triphenylphosphine or 1,3-cyclocarbodiimide and an organic base such as triethylamine or pyridine. It is prefer to carry this reaction at the temperature of 0–100° C. in an inert solvent such as ethers like tetrahydrofuran, ethyethyl acetate, acetonitrile, toluene, xylene, hexane, methylene chloride, carbon tetrachloride, dichloroethane or the like. The product is obtained by evaporating a solvent and performing column chromatograph.

Another method for preparing the compounds (1) represented in the following scheme 2 is an alkylation of a compound of formula 9 with compounds of formula 10.

Scheme 2

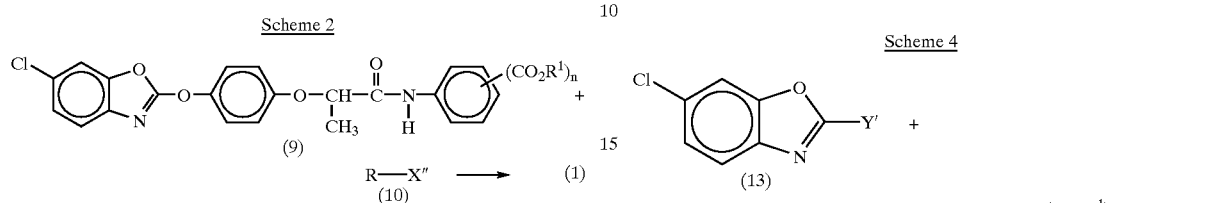

wherein, X″, which is a leaving group, is Cl, Br, I, benzenesulfonyloxy, toluenesulfonyloxy, methanesulfonyloxy or lower alkyl sulfate group; R, $R^1$ and n are the same as previously defined.

In scheme 2, it is prefer to use a strong base which is enough to pull out a hydrogen from anilide, NH. The strong base used in this invention is NaOH, KOH, LiOH, NaH, n-BuLi or LDA. It is prefer to carry this reaction at the temperature of −78–50° C. in an inert solvent such as ethers like ethylether, dioxane or tetrahydrofuran or hydrocarbons like hexane.

Another method for preparing the compounds (1) represented in the following scheme 3 is a condensation reaction of a compound of formula 11 with a compound of formula 12 in the presence of a base.

Scheme 3

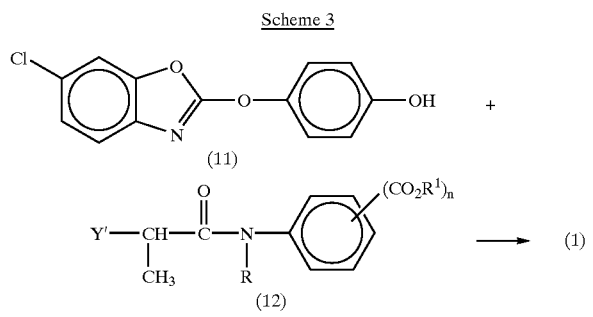

wherein, Y′ is a halogen atom, alkylsulfonyloxy, haloalkylsulfonyloxy, benzenesulfonyloxy or toluenesulfonyloxy group; R, $R^1$ and n are the same as previously defined.

In Scheme 3, it is prefer to use alkali metal hydroxides such as sodium hydroxide or potassium hydroxide, alkali metal carbonates such as sodium carbonate or potassium carbonate, alkali metal hydrogencarbonates such as sodium hydrogencarbonate or potassium hydrogencarbonzate or organic bases such as triethylamine, N,N-dimethylaniline, pyridine or 1,8-diazabicyclo[5,4,0]undec-7-ene.

A phase transition catalyst such as tetra-n-butylammonium bromide or 18-crown-6-[1,4,7,10,13,16-hexaoctacyclooctadecane] can be added to complete a reaction rapidly, if necessary. And also one or more than two solvents can be combined and used, if deemed necessary. It is prefer to use an inert organic solvent; for example; ketones such as acetone; aromatic hydrocarbons such as toluene, xylene or chlorobenzene; aliphatic hydrocarbons such as petroleum ether or ligroin; ethers such as diethylether, tetrahydrofuran or dioxane; nitriles such as acetonitrile or propionitrile; or amides such as N,N-dimethylformamide, N,N-dimethylacetamide, N-methylpyrrolidone. A reaction is carried at the temperature of from 0° C. to reflux, preferably 25~100° C. for 1 to 24 hour(s) to afford a high yield.

Another method for preparing the compound (1) represented in the following scheme 4 is a condensation reaction of a compound of formula 13 with a compound of formula 14 in the presence of a base.

Scheme 4

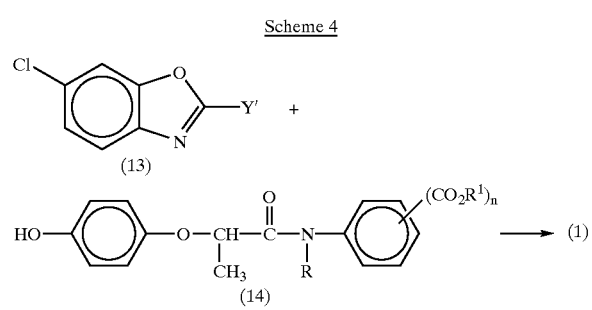

wherein, $Y^1$, R, $R^1$ and n are the same as previously defined.

In Scheme 4, it is prefer to use inorganic bases; for example; alkali metal hydroxides such as sodium hydroxide or potassium hydroxide, alkali metal carbonates such as sodium carbonate or potassium carbonate, alkali metal hydrogencarbonates such as sodium hydrogencarbonate or potassium hydrogencarbonate or organic bases such as triethylamine, N,N-dimethylaniline, pyridine, picoline, quinoline, or 1,8-diazabicyclo[5,4,0]undec-7-ene.

A phase transition catalyst such as tetra-n-butylammonium bromide or 18-crown-6[1,4,7,10,13,16-hexaoctacyclooctadecane] can be used, if necessary. And also one or more than two solvents can be combined and used, if deemed necessary. It is prefer to use an inert organic solvent; for example; ketones such as acetone or butanone; aromatic hydrocarbons such as benzene, toluene, xylene or chlorobenzene; aliphatic hydrocarbons such as petroleum ether, or ligroin; ethers such as diethylether, tetrahydrofuran or dioxane; nitriles such as acetonitrile or propionitrile; or amides such as N,N-dimethylformamide, N,N-dimethyl acetamide or N-methylpyrrolidone. A reaction is carried at the temperature of from 0° C. to reflux, preferably 20~100° C. for 1 to 24 hour(s) to afford a high yield.

The above reactions lead to the compound of formula 1 and more particularly, typical hydrolysis of ether group leads the product when $R^1$ is a hydrogen atom.

The present invention is explained in more detail by the following examples but is not limited by these examples.

EXAMPLE 1

N-(3-ethoxycarbonyphenyl)-2-bromo-propionamide

2-Bromopropionic acid(3.4 g, 0.022 mol) and 3-aminobenzoic acid ethylester(3.96 g, 0.024 mol) were dissolved in 50 ml of chloroform and cooled to 0° C. Dicyclohexylcarbodiimide(5 g, 0.024 mol) dissolved in 10 ml of chloroform was slowly injected through a syringe. A temperature of the reaction mixture was raised to room temperature and it was stirred for 1 hour. Solid remained during the reaction was filtered out and washed twice with 20 ml of chloroform. The filtrate was concentrated under reduced pressure and the crude product was purified by column chromatography (eluent; ethyl acetate/n-hexane=1/5) to afford 5.2 g of the target product.

$^1$H-NMR(CDCl$_3$): δ1.39(3H, t), 1.95(3H, d), 4.36(2H, q), 4.58(1H, q), 7.37~8.08(4H, m), 8.45(1H, br)

EXAMPLE 2

N-(3-ethoxycarbonyphenyl)-2-(4-hydroxyphenoxy) propionamide

N-(3-ethoxycarbophenyl)-2-bromo-propionamide(30 g, 0.1 mol), hydroquinone(10 g, 0.091 mol), potassium carbonate(15.2 g, 0.11 mol) and tetra-n-butylammonium bromide(1.5 g) were dissolved in 500 ml of acetonitrile and heated at reflux for 10 hours. The reaction mixture was cooled to room temperature and solid remained during the reaction was filtered out. The filtrate was concentrated under reduced pressure and the crude product was purified by column chromatography(eluent ethyl acetate/n-hexane=1/2) to afford 27 g of the target product $^1$H-NMR(CDCl$_3$): δ1.38(3H, t), 1.58(3H, d), 4.34(2H, q), 4.65(1H, q), 6.7~8.27(8H, m), 8.4(1H, br)

EXAMPLE 3

2-[4-(6-chloro-2-benzoxazoyloxy)-phenoxy] propionic acid-N-(3-ethoxycarbonyphenyl)amide N-(3-ethoxycarbonylphenyl)-2-(4-hydroxyphenoxy) propionamide (13.2 g, 0.04 mol), 2,6-dichlorobenzoxazole (6.85 g, 0.036 mol), potassium carbonate (6 g, 0.043 mol) and tetra-n-butylammonium bromide (1 g) were dissolved in 250 ml of acetonitrile and heated at reflux for 6 hours. The reaction mixture was cooled to room temperature and solid remained during the reaction was filtered out. The filtrate was concentrated under reduced pressure and the crude product was purified by column chromatography (eluent:ethyl acetate/n-hexane=1/4) to afford 14.2 g of the target product.

$^1$H-NMR(CDCl$_3$): δ1.4(3H, t), 1.67(3H, d), 4.4(2H, q), 4.8(1H, q), 7.05~8.04(11H, m), 8.29(1H, br)

EXAMPLE 4

2-[4-(6-chloro-2-benzoxazoyloxy)-phenoxy] propionic acid-N-(3-ethoxycarbonyphenyl)amide 3-aminobenzoic acid ethylester(165.19 mg, 1 mmol), triphenylphosphine(393.4 mg, 1.5 mmol), triethylamine (0.15 ml, 1 mmol) and carbon tetrachloride(1 ml) were added sequentially to 2-[4-(6-chloro-2-benzoxazoyloxy)-phenoxy]propionic acid (346.7 mg, 1 mmol) dissolved in 10 ml of tetrahydrofuran. The reaction mixture was heated at reflux for 6 hours. The reaction mixture was cooled to room temperature and acidified with 5% hydrochloric acid, followed by addition of water. The acidified reaction mixture was extracted three times with ethyl acetate. The combined organic solvent layer was dried over magnesium sulfate, filtered and concentrated under reduced pressure. The crude product was purified by column chromatography (eluent:ethyl acetate/n-hexane=1/4) to afford 250 mg of the target product.

$^1$H-NMR(CDCl$_3$): δ1.4(3H, t), 1.67(3H, d), 4.4(2H, q), 4.8(1H, q), 7.05~8.04(11H, m), 8.29(1H, br)

EXAMPLE 5

2-[4-(6-chloro-2-benzoxazoyloxy)-phenoxy] propionic acid-N-(3-ethoxycarbonyphenyl)amide 2-[4-(chloro-2-benzoxazoyloxy)-phenoxy]propionic acid (0.693 g, 2 mmol) was dissolved in 20 ml of benzene and SOCl$_2$(6 ml) was added, followed by heating at reflux for 10 hours. Benzene and excess of SOCl2 were removed by evaporation under reduced pressure. Anhydrous tetrahydrofuran(10 ml) and 3-aminobenzoic acid ethylester (0.33 g, 2 mmol) dissolved in anhydrous tetrahydrofuran(10 ml) were added slowly to the reaction mixture at 0° C. The reaction mixture was stirred for 30 min at 0° C. and additionally stiffed at room temperature for 1 hour. The reaction mixture was extracted three times with ethyl acetate. The combined organic solvent layer was dried over magnesium sulfate, filtered and concentrated under reduced pressure. The crude product was purified by column chromatography(eluent:ethyl acetate/n-hexane=1/4) to afford 0.75 g of the target product.

EXAMPLE 6

2-[4-(6-chloro-2-benzoxazoyloxy)-phenoxy] propionic acid-N-(3-ethoxycarbonyphenyl)-N-methylamide 2-[4-(6-chloro-2-benzoxazoyloxy)-phenoxy]propionic acid-N-(3-ethoxycarbonyphenyl)amide (5.4 g, 11.2 mmol) was dissolved in 10 ml of anhydrous tetrahydrofuran and cooled to 0° C. 60% NaH(0.98 g, 24.4 mmol) and (CH3)$_2$SO$_4$(1.41 g, 11.2 mmol) were added sequentially by keeping the temperature of 0° C. The reaction mixture was stirred at room temperature for 2 hours. After reaction was completed, it was cooled to 0° C. and acidified with 3% of hydrogen chloride. Ice water was poured to the reaction mixture and it was extracted three times with ethyl acetate. The combined organic solvent layer was dried over magnesium sulfate, filtered and concentrated under reduced pressure. The crude product was purified by column chromatography(eluent:ethyl acetate/n-hexane=1/2) to afford 3.2 g of the target product.

EXAMPLE 7

2-[4-(6chloro-2-benzoxazoyloxy)-phenoxy] propionic acid-N-(3-methoxycarbonyphenyl)amide 2-[4-(6-chloro-2-benzoxazoyloxy)-phenoxy]propionic acid (346.7 mg, 1 mmol) and 3-aminobenzoic acid methylester(151.2 mg, 1 mmol) were dissolved in 15 ml of tetrahydrofuran and the reaction mixture was cooled to −5° C. 1,3-dicyclohexylcarbodiimide(226 mg, 1.1 mmol) was added to it. A temperature of the reaction mixture was raised to room temperature and it was stirred for 2 hours. Solid remained during the reaction was filtered out and washed twice with 10 ml of tetrahydrofuran. The filtrate was concentrated under reduced pressure and the crude product was purified by column chromatography (eluent; ethyl acetate/n-hexane=1/4) to afford 280 mg of the target product. m.p.: 135–140° C.;

$^1$H-NMR(CDCl$_3$): δ1.67(3H, d), 3.92(3H, s), 4.8(1H, q), 7.05~8.08(11H, m), 8.29(1H, br)

EXAMPLES 8–11

The compounds represented in the following Table 2 were prepared by the same procedure of example 7 except using of corresponding aminobenzoic acid esters instead of 3-aminobenzoic acid methylester.

TABLE 2

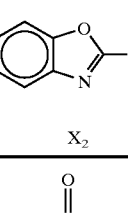

| Example | X₁ | X₂ | X3 | ¹H-NMR(CDCl₃) | m.p. (° C.) |
|---|---|---|---|---|---|
| Example 8 | H | —C(=O)—O-n | H | 1.03(3H, t), 1.67(3H, d), 1.78(2H, m), 4.29(2H, t), 4.8(1H, q), 7.05~8.04(11H, m), 8.29(1H, br) | 104–106 |
| Example 9 | H | —C(=O)—O-i- | H | 1.37(6H, d), 1.67(3H, d), 4.8(1H, q), 5.25(1H, m), 7.02~8.01(11H, m), 8.3(1H, br) | 104–105 |
| Example 10 | H | H | —C(=O)—O—M | 1.67(3H, d), 3.91(3H, s), 4.8(1H, q), 7.02~7.46(7H, m), 7.68(2H, d), 8.04(2H, d), 8.3(1H, br) | 183–184 |
| Example 11 | H | H | —C(=O)—O—Et | 1.41(3H, t), 1.67(3H, d), 4.38(2H, q), 4.8(1H, q), 7.02~7.46(7H, m), 7.68(2H, d), 8.04(2H, d), 8.3(1H, br) | 136–138 |

Formulation

In order to use the compounds according to the present invention as herbicides, they should be formulated in such a suitable type such as wettable powder, emulsions, granules, suspensions and solutions by combining a carrier, a surfactant, a dispersing agent or a supplement agent. Many of these may be applied directly or after diluted with suitable media. Formulations can be prepared at spray volume of from hundreds liters to thousands liters per hectare. The formulations contain about 0.1% to 99% by weight of active ingredient(s) wherein 0.1% to 20% of surfactant(s) or 0% to 99.9% of solid or liquid diluent(s) are recommended to be added. The formulations will contain these ingredients in the following approximate proportions shown in Table 3.

TABLE 3

| | Weight % | | |
|---|---|---|---|
| Formulations | Active ingredient | Diluent | Surfactant |
| Wettable powders | 10~90 | 0~74 | 1~10 |
| Suspension | 3~50 | 40~95 | 0~15 |
| Emulsions · Solution | 3~50 | 40~95 | 0~15 |
| Granules | 0.1~95 | 5~99.9 | 1~15 |

The proportion of active ingredients is depending on the intended use. Higher ratios of a surfactant to active ingredients are sometimes desirable and are achieved by incorporation into the formulation or tank mixing.

Solid diluents with high absorption are preferred for wettable powders. Liquid diluents and solvents are preferably stable against phase separation at 0° C. All the formulations may contain a small amount of additives to prevent forming, caking, corrosion and growth of microorganisms.

According to conventional methods to prepare a composition, solutions can be made only by blending ingredients and fine solids by blending and pulverizing with hammer-mill. Suspensions can be made by wet-milling and granules can be made by spraying the active ingredients on performed granular carrier.

Preparation examples of typical formulations are as follows.

Formulation 1: Wettable powders

The ingredients are thoroughly blended, re-blended after spraying liquid surfactant on the solid ingredients and hammer-milled until all the solids are essentially under 100 μm.

| | |
|---|---|
| Active ingredient (Example 3 Compound) | 20 wt % |
| Dodecylphenol polyethylene glycol ether | 2 wt % |
| Sodium ligninsulfonate | 4 wt % |
| Sodium silicon aluminate | 6 wt % |
| Montmorillonite | 68 wt % |

Formulation 2: Wettable powders

The ingredients are blended, hammer-milled until all the solids are under 25 μm and packaged.

| | |
|---|---|
| Active ingredient (Example 3 Compound) | 80 wt % |
| Sodium alkyl naphthalenesulfonate | 2 wt % |
| Sodium ligninsulfonate | 2 wt % |
| synthetic amorphous silica | 3 wt % |
| Kaolinite | 13 wt % |

Formulation 3: Emulsions

The ingredients are mixed and homogeneously dissolved to give emulsions.

| | |
|---|---|
| Active ingredient (Example 3 Compound) | 30 wt % |
| Cyclohexanone | 20 wt % |
| Polyoxyethylene alkylaryl ether | 11 wt % |

-continued

| Calcium alkylbenzenesulfonate | 4 wt % |
| Methylnaphthalene | 35 wt % |

Formulation 4: Granules

The ingredients were thoroughly blended. 20 Weight part of water was added to 100 weight part of the ingredient mixture. The ingredient mixture was granulated with a size of 14 to 32 mesh by using extrusive granulator and dried.

| Active ingredient (Example 3 Compound) | 5 wt % |
| Sodium laurylalcoholsulfonate | 2 wt % |
| Sodium ligninsulfonate | 5 wt % |
| Carboxymethyl cellulose | 2 wt % |
| Potassium sulfate | 16 wt % |
| Plaster | 70 wt % |

The formulations according to this invention were sprayed with diluting to a certain concentration.

UTILITY

The compounds according to the present invention represent high activity as leaf treatment herbicides for rice and especially effective in rice due to an excellent control of barnyard grass.

The active ingredients can be used from 30 g to 1 kg per hectare, preferably from 50 g to 400 g. The amount of the compounds of the present invention depends on amount and size of weeds and formulations. The herbicides of the present invention can be used as alone or in combination with other herbicides, insecticides or bactericides. Especially it is essential to add one or more of agents selected from the group consisting of bentazon, quinclorac, propanil, simetryn, 2,4-D, fenoxaprop-ethyl, linuron, MCPA, azafenidin, carfentrazone, molinate, thiobencarb, pendimethalin, bensulfuron-methyl, pyrazosulfuron-ethyl, metsulfuron-methyl, thifensulfuron-methyl, tribenuron-methyl, trifluralin, amidosulfuron, bromoxynil, butachlor, mecoprop, metribuzin, bifenox, benfuresate, isoproturon, cyhalofop-butyl, mefenaset, fentrazamide, pyriminobac-methyl, bispyribac sodium, azimsulfruon, cyclosulfamuron and pyanchor.

The herbicidal effect of the compounds of this invention was tested and the examples are as follows.

Experimental Example 1

Leaf Treatment Test

Seeds of rice, wheat, barley, corn, cotton, barnyard grass, common sorgum, large crabgrass and fall panicum were seeded at a pot with a surface area of 600 cm. When barnyard grass kept at 20~30° C. had three leaves, wettable powders prepared by mixing 1 weight part of the active compound, 5 weight part of acetone and 1 weight part of emulsifier and diluting with water was applied directly on the leaves in 2000 l per hectare. The concentration of the spray liquid was so chosen the particular amounts of the active compound desired. 14 days after the treatment, the degree of damage to the plants was rated in % damage in comparison to the development of untreated control.

0% no action (like untreated control)
20% slight effect
70% herbicidal effect
100% total destruction In the test, the active compound(s) of formula 1 according to the invention exhibited an excellent selectivity toward the plants and herbicidal activity against weeds.

The plants employed in this test are in table 4.

TABLE 4

| ABRV. | SCIENTIFIC NAME | ENGLISH NAME |
| --- | --- | --- |
| ZEAMX | Zea mays L. | Corn |
| GLXMA | Glydne max (L.) MERR | Soy bean |
| GOSHI | Gossypium | Cotton |
| TRZAW | Triticum aestivum L. | Wheat |
| ORYSA | Oryza sativa L. cv. Dongjin | Rice |
| SORBI | Andropogon sorghum | Common sorgum |
| ECHCG | Echinochloa crus-galli Beauv. var. caudata Kitagawa | Barnyard grass |
| DIGSA | Digitaria Sanguinalis (L.) SCOP | Large crabgrass |
| PANDI | Panicum dichotomiflorum Michx | Fall panicum |

Among the compounds of formula 1, herbicidal activity of the compounds in table 5 is represented in the following tables 6, 7 and 8.

TABLE 5

Cl—[benzoxazole]—O—[phenyl]—O—CH(CH$_3$)—C(=O)—NH—[phenyl with X$_1$, X$_2$, X$_3$]

| Compound No. | R | X$_1$ | X$_2$ | X$_3$ |
| --- | --- | --- | --- | --- |
| 1 | H | H | —C(=O)—O—Me | H |
| 2 | H | H | —C(=O)—O—Et | H |
| 3 | CH$_3$ | H | —C(=O)—O—Et | H |
| 4 | H | H | H | —C(=O)—O—Me |
| 5 | H | H | H | —C(=O)—O—Et |
| 6 | H | H | —C(=O)—O—n-Pr | H |
| 7 | H | H | —C(=O)—O—i-Pr | H |
| control | H | H | 3-CH$_3$ | H |

TABLE 6

| Compound | Treated amount (g/ha) | ORYSA | ECHCG |
| --- | --- | --- | --- |
| 1 | 15 | 0 | 0 |
|   | 30 | 0 | 80 |
|   | 60 | 0 | 100 |
|   | 125 | 0 | 100 |

TABLE 6-continued

| Compound | Treated amount (g/ha) | ORYSA | ECHCG |
|---|---|---|---|
|  | 250 | 10 | 100 |
|  | 500 | 20 | 100 |
|  | 1000 | 30 | 100 |
| 2 | 15 | 0 | 8 |
|  | 30 | 0 | 100 |
|  | 60 | 0 | 100 |
|  | 125 | 0 | 100 |
|  | 250 | 15 | 100 |
|  | 500 | 35 | 100 |
|  | 1000 | 45 | 100 |
| 3 | 15 | 0 | 0 |
|  | 30 | 0 | 0 |
|  | 60 | 0 | 20 |
|  | 125 | 0 | 90 |
|  | 250 | 0 | 100 |
|  | 500 | 0 | 100 |
|  | 1000 | 0 | 100 |

TABLE 7

| Compound | Weeds | Treated amount (kg/ha) | |
|---|---|---|---|
|  |  | 0.1 | 0.025 |
| 4 | ZEAMX | 0 | 0 |
|  | GLXMA | 0 | 0 |
|  | GOSHI | 0 | 0 |
|  | TRZAW | 0 | 0 |
|  | ORYSA | 30 | 0 |
|  | SORBI | 100 | 70 |
|  | ECHCG | 100 | 100 |
|  | DIGSA | 100 | 100 |
|  | PANDI | 100 | 80 |
| 5 | ZEAMX | 30 | 0 |
|  | GLXMA | 20 | 0 |
|  | GOSHI | 0 | 0 |
|  | TRZAW | 20 | 0 |
|  | ORYSA | 40 | 0 |
|  | SORBI | 100 | 95 |
|  | ECHCG | 100 | 95 |
|  | DIGSA | 100 | 100 |
|  | PANDI | 100 | 95 |

TABLE 8

| Compound | Weeds | Treated amount (kg/ha) | | | | |
|---|---|---|---|---|---|---|
|  |  | 1 | 025 | 0.063 | 0.016 | 0.004 |
| 2 | ZEMAX | 100 | 100 | 20 | 0 | 0 |
|  | GLXMA | 0 | 0 | 0 | 0 | 0 |
|  | GOSHI | 0 | 0 | 0 | 0 | 0 |
|  | TRZAW | 40 | 20 | 0 | 0 | 0 |
|  | ORYSA | 40 | 40 | 0 | 0 | 0 |
|  | SORBI | 100 | 100 | 100 | 100 | 40 |
|  | ECHCG | 100 | 100 | 100 | 100 | 90 |
|  | DIGSA | 100 | 100 | 100 | 100 | 95 |
|  | PANDI | 100 | 100 | 100 | 100 | 95 |

As a result of these tests, the compounds of the present invention exhibit an excellent selectivity toward rice and herbicidal activity against barnyard grass. And also it is proved that the compounds are very stable for the beans, potatoes, vegetables and useful to control weeds.

What is claimed is:

1. A herbicidal compound of formula 1,

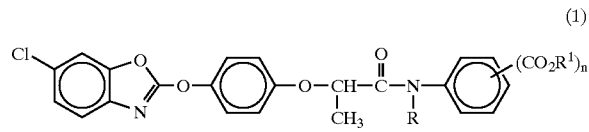

(1)

wherein

R is a hydrogen atom, methyl or ethyl group;

$R^1$ is a hydrogen atom, $C_1$–$C_6$ alkyl, $C_1$–$C_6$ alkyl substituted with 1 to 3 of the group consisting of hydroxy, carboxyl, and a halogen atom, $C_3$–$C_6$ cycloalkyl, $C_3$–$C_4$ alkenyl, $C_3$–$C_4$ alkinyl, or $C_2$–$C_4$ alkoxyalkyl group;

n is an integer of 1 or 2 and when n is 2, $R^1$ can be a combination of other substituents.

2. The herbicidal compound as defined in claim 1, wherein said R is a hydrogen atom or methyl group; said $R^1$ is a hydrogen atom, methyl or ethyl group; and said n is 1.

3. The herbicidal compound as defined in claim 1, wherein said R is a hydrogen atom or methyl group; said $R^1$ is methyl or ethyl group; n is 1; said $CO_2R^1$ is substituted on 3- or 4-position.

4. The herbicidal compound as defined in claim 1, wherein said R is a hydrogen atom; said $R^1$ is methyl or ethyl group; n is 1; said $CO_2R^1$ is substituted on 3-position.

5. The herbicidal compound as defined in claim 1, wherein said R is a hydrogen atom; said $R^1$ is ethyl group; n is 1; said $CO_2R^1$ is substituted on 3-position.

6. A method to control barnyard grass produced from growing rice without any harm by applying the compounds of formula 1 with effective amount,

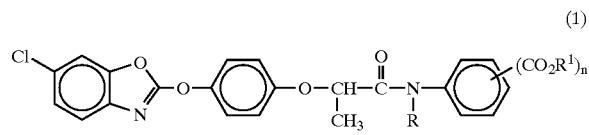

(1)

wherein, R, $R^1$ and n are the same as defined in claim 1.

7. The method to control barnyard grass as defined in claim 6, wherein said R is a hydrogen atom or methyl group; said $R^1$ is a hydrogen atom or ethyl group; n is 1; said $CO_2R^1$ is substituted on 3- or 4-position.

8. The method to control barnyard grass as defined in claim 6, wherein said R is a hydrogen atom or methyl group; said $R^1$ is methyl or ethyl group; n is 1; said $CO_2R^1$ is substituted on 3- or 4-position.

9. The method to control barnyard grass as defined in claim 6, wherein said R is a hydrogen atom; said $R^1$ is methyl or ethyl group; n is 1; said $CO_2R^1$ is substituted on 3-position.

10. The method to control barnyard grass as defined in claim 6, wherein said R is a hydrogen atom; said $R^1$ is ethyl group; n is 1; said $CO_2R^1$ is substituted on 3-position.

11. The herbicidal composition comprising the compound of formula 1 and agriculturally acceptable carrier, supplement agent, surfactant or other herbicidal compounds,

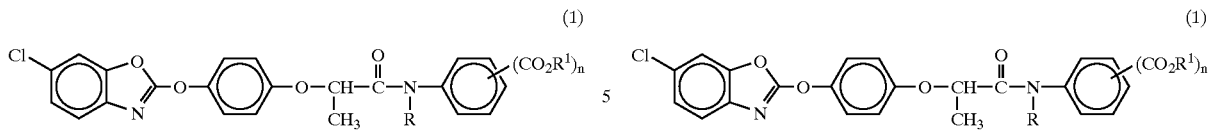

wherein R, $R^1$ and n are the same as defined in claim 1.

12. The herbicidal composition as defined in claim 11, wherein said R is a hydrogen atom or methyl group; said $R^1$ is methyl or ethyl group; and n is 1.

13. The herbicidal composition as defined in claim 11, wherein said R is a hydrogen atom or methyl group; said $R^1$ is methyl or ethyl group; n is 1; and said $CO_2R^1$ is substituted on 3- or 4-position.

14. The herbicidal composition as defined in claim 11, wherein said R is a hydrogen atom; said $R^1$ is methyl or ethyl group; n is 1; and said $CO_2R^1$ is substituted on 3-position.

15. The Herbicidal composition as defined in claim 11, wherein said R is a hydrogen atom; said $R^1$ is ethyl group; n is 1; and said $CO_2R^1$ is substituted on 3-position.

16. A method for preparing the compound of formula 1 by reacting the compound of formula 7 and the compound of formula 8,

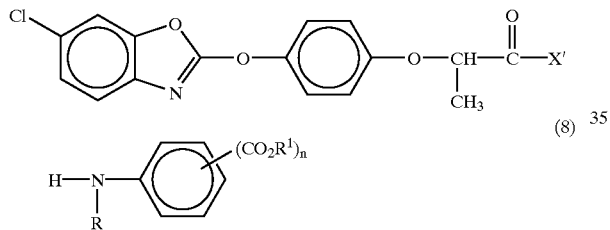

wherein R, $R^1$ and n are the same as defined in claim 1; and X is OH, Br, or phenoxy group.

17. A method for preparing the compound of formula 1 by reacting the compound of formula 9 and the compound of formula 10,

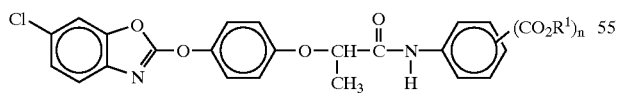

wherein R, $R^1$ and n are the same as defined in claim 1; and X", which is a leaving group, is Cl, Br, I benzenesulfonyloxy, toluenesulfonyloxy, methanesulfonyloxy or lower alkyl sulfate group.

18. A method for preparing the compound of formula 1 by reacting the compound of formula 11 and the compound of formula 12,

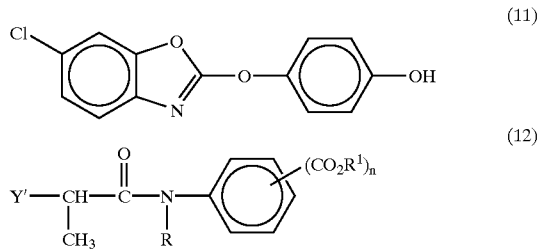

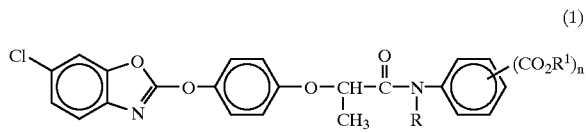

wherein R, $R^1$ and n are the same as defined in claim 1; and Y' is a halogen atom, alkylsulfonyloxy, haloalkylsulfonyloxy, benzenesulfonyloxy or toluenesulfonyloxy group.

19. A method for preparing the compound of formula 1 by reacting the compound of formula 13 and the compound of formula 14,

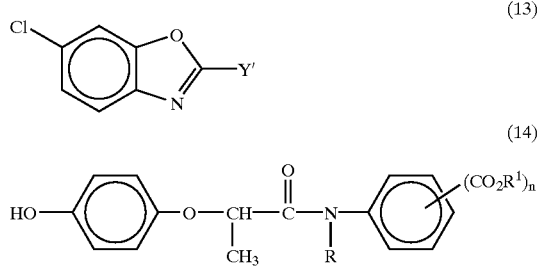

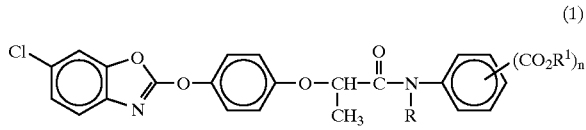

wherein R, $R^1$ and n are the same as defined in claim 1; and Y' is a halogen atom, alkylsulfonyloxy, haloalkylsulfonyloxy, benzenesulfonyloxy or toluenesulfonyloxy group.

* * * * *